United States Patent
Hoover et al.

(10) Patent No.: US 9,574,911 B2
(45) Date of Patent: Feb. 21, 2017

(54) TWO-CORE OPTICAL FIBERS FOR DISTRIBUTED FIBER SENSORS AND SYSTEMS

(71) Applicants: Brett Jason Hoover, Middlebury Center, PA (US); Ming-Jun Li, Horseheads, NY (US); Shenping Li, Painted Post, NY (US)

(72) Inventors: Brett Jason Hoover, Middlebury Center, PA (US); Ming-Jun Li, Horseheads, NY (US); Shenping Li, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 714 days.

(21) Appl. No.: 13/658,991

(22) Filed: Oct. 24, 2012

(65) Prior Publication Data
US 2014/0042306 A1    Feb. 13, 2014

Related U.S. Application Data

(60) Provisional application No. 61/681,402, filed on Aug. 9, 2012.

(51) Int. Cl.
*G02B 6/02*    (2006.01)
*G01J 1/04*    (2006.01)
(Continued)

(52) U.S. Cl.
CPC ...... *G01D 5/35364* (2013.01); *G01D 5/35303* (2013.01); *G01D 5/35383* (2013.01);
(Continued)

(58) Field of Classification Search
CPC . G02B 6/02042; G02B 6/0281; G02B 6/0365; G02B 6/03644; G02B 6/262; G02B 6/036; G02B 6/12004; G01B 11/16; G01B 11/18; G01J 5/0821; G01D 5/35364; G01K 11/32; G01K 2011/322; C03C 13/046; G01L 1/242
(Continued)

(56) References Cited

U.S. PATENT DOCUMENTS 4,822,126 A * 4/1989 Sweeny ............... G02B 6/2835
                                                  385/43
5,696,863 A    12/1997 Kleinerman
(Continued)

FOREIGN PATENT DOCUMENTS

CA    2629446    10/2009
EP    2110651    10/2009

OTHER PUBLICATIONS

Tjugiarto T et al: "Bandpass Filtering Effect in Tapered Asymmetrical Twin-Core Optical Fibers", Electronic Letters, IEE Stevenage, GB, vol. 29, No. 12, Jun. 10, 1993 (Jun. 10, 1993), pp. 1077-1078, XP000373162, ISSN: 0013-5194.
(Continued)

*Primary Examiner* — Akm Enayet Ullah
*Assistant Examiner* — Michael Mooney
(74) *Attorney, Agent, or Firm* — Svetlana Z. Short

(57) ABSTRACT

A two-core optical fiber is provided for use in Brillouin distributed fiber sensor applications and systems. The two-core fiber includes a first and second core. Each core is configured to exhibit a Brillouin frequency shift greater than 30 Mhz relative to the other core. Further, each core possesses temperature and strain coefficients that differ from the other core. The cores can be configured to produce Brillouin frequency shift levels of at least 30 Mhz relative to one another. These differences in shift levels may be effected by adjustment of the material compositions, doping concentrations and/or refractive index profiles of each of the cores.
(Continued)

These optical fibers may also be used in BOTDR- and BOTDA-based sensor systems and arrangements.

20 Claims, 3 Drawing Sheets

(51) Int. Cl.

| | |
|---|---|
| G01D 5/353 | (2006.01) |
| G01J 5/08 | (2006.01) |
| G01K 11/32 | (2006.01) |
| G02B 6/028 | (2006.01) |
| G02B 6/036 | (2006.01) |

(52) U.S. Cl.
CPC ............ *G01J 5/0821* (2013.01); *G01K 11/32* (2013.01); *G02B 6/02042* (2013.01); *G02B 6/0281* (2013.01); *G02B 6/0365* (2013.01)

(58) Field of Classification Search
USPC ............... 385/12, 13, 14, 39, 123–127, 141; 356/32, 34, 35.5, 320; 250/227.14, 227.18
See application file for complete search history.

(56) References Cited

U.S. PATENT DOCUMENTS

| | | | |
|---|---|---|---|
| 7,543,982 B2* | 6/2009 | Yamamoto | G01B 11/18 356/32 |
| 7,599,047 B2* | 10/2009 | Zou | G01B 11/18 356/32 |
| 2002/0176677 A1 | 11/2002 | Kumar et al. | |
| 2008/0273852 A1 | 11/2008 | Parker | |
| 2011/0052129 A1 | 3/2011 | Sasaoka | |
| 2011/0119023 A1* | 5/2011 | Duindam | A61B 19/22 702/150 |
| 2013/0021615 A1* | 1/2013 | Duncan | G01H 9/004 356/477 |

OTHER PUBLICATIONS

Bao et al., "Combined distributed temperature and strain sensor based on Brillouin loss in an optical fiber", Optics Letters, vol. 19, No. 2, Jan. 15, 1994, pp. 141-143.

Bao et al., "Recent Progress in Brillouin Scattering Based Fiber Sensors", Sensors 2011, 11, pp. 4152-4187.

Geng et al., "Distributed fiber temperature and strain sensor using coherent radio-frequency detection of spontaneous Brillouin scattering", Applied Optics, vol. 46, No. 23, Aug. 10, 2007, pp. 5928-5932.

Gruner-Nielsen et al., Source: "Silica-based highly nonlinear fibers with a high SBS threshold", 2011 IEEE Winter Topicals (WTM), 2011, pp. 171-172.

Horiguchi et al., "Development of a distributed sensing technique using Brillouin scattering", Journal of Lightwave Technology, vol. 13, No. 7, 1995, pp. 1296-1302.

Kee et al., "Low-loss, low-cost spontaneous Brillouin-based system for simultaneous distributed strain and temperature sensing," Conference on Lasers and Electro-Optics (CLEO 2000), Technical Digest, Postconference Edition, TOPS vol. 39, May 7-12, 2000, p. 432.

Lee et al., "Utilization of a dispersion-shifted fiber for simultaneous measurement of distributed strain and temperature through Brillouin frequency shift", IEEE Photonics Technology Letters, vol. 13, No. 10, Oct. 2001, pp. 1094-1096.

Posey et al., "Simultaneous measurements of temperature and strain using stimulated Brillouin scattering in GeO2-doped core and dispersion shifted fiber," IEICE Transactions on Electronics, vol. E83-C, No. 3, Mar. 2000, pp. 413-417.

Soto et al., "Enhanced simultaneous distributed strain and temperature fiber sensor employing spontaneous Brillouin scattering and optical pulse coding", IEEE Photonics Technology Letters, vol. 21, No. 7, Apr. 1, 2009, pp. 450-452.

Zou et al., "Complete discrimination of strain and temperature using Brillouin frequency shift and birefringence in a polarization-maintaining fiber," Optics Express, vol. 17, No. 3, Feb. 2, 122009, pp. 1248-1255.

Zou et al., "Dependence of the Brillouin frequency shift on strain and temperature in a photonic crystal fiber", Optics Letters, vol. 29, No. 13, Jul. 1, 2004, pp. 1485-1487.

Anon: "Fibre optics give the inside story", Enginnering, vol. 227 No. 12 (1987) p. 17 XP008165343.

Horiguchi et al. "Invited Paper: Measurement of temperature and strain distribution by Brillouin frequency shift in silica optical fibers", Proceedings of the SPIE—the International Society for Optical Engineering, vol. 1797 (1993) p. 2-13 XP008165343.

International Search Report and Written Opinion PCT/US2013/053228 Dated Nov. 6, 2013.

Kwon et al. "Analysis of brillouin frequency shift and longitudinal acoustic wave in a silica optical fiber with a triple-layered structure", Journal of Lightwave Technology. vol. 21 No. 8 (2003) p. 1779-1786 XP011099431.

Wylie et al. "Fiber Optic Distributed Differential Displacement Sensor", Journal of Lightwave Technology, vol. 29 No. 18 (2011) p. 2847-2852 XP011359080.

\* cited by examiner

TWO-CORE OPTICAL FIBERS FOR DISTRIBUTED FIBER SENSORS AND SYSTEMS

CROSS-REFERENCE TO RELATED APPLICATIONS

This application claims priority under 35 U.S.C. §119(e) to U.S. Provisional Patent Application No. 61/681,402, filed Aug. 9, 2012, entitled "TWO-CORE OPTICAL FIBERS FOR DISTRIBUTED FIBER SENSORS AND SYSTEMS," which is herein incorporated by reference in its entirety.

FIELD

The disclosure generally relates to sensing systems and methods, and in particular relates to distributed Brillouin sensing systems and methods that use a two-core optical fiber.

BACKGROUND

Distributed Brillouin fiber sensors are rapidly being adopted for many applications, including but not limited to, structure health monitory (SHM), geotechnical engineering, power lines, oil and gas pipe lines, and oil drilling. Brillouin-based sensor technology operates in two regimes: (a) stimulated Brillouin scattering (i.e., Brillouin optical time domain analysis, or BOTDA); and (b) spontaneous Brillouin scattering (i.e., Brillouin optical time domain reflectometry, or BOTDR). Both BOTDA and BOTDR regimes utilize the linear dependence of the Brillouin frequency shift on temperature and/or strain of the tested component(s).

One problem with the implementation of distributed Brillouin fiber sensors is the sensitivity of the Brillouin frequency shift (BFS) to both strain and temperature. This effect leads to ambiguity in the measurements. In particular, conventional approaches fail to isolate the change in strain and/or temperature of the tested component(s) associated with an observed BFS.

One approach used to address this problem is the use of two fibers placed adjacent to each other, in which one fiber is isolated from any strain effects. The isolated fiber can be used to monitor the temperature, while the other fiber will measure the effect of both strain and temperature. However, this approach is subject to at least two types of measurement errors. First, the isolated fiber is not totally strain free, which results in measurement errors associated with temperature. Second, the different length of the two fibers from the input to the sensing location results in measurements at two different locations, leading to additional measurement errors.

In another two-fiber approach, two fibers with different Brillouin properties are used to sense both temperature and strain. As such, the BFSs of the two fibers are measured. The temperature and strain levels are calculated based on the coefficients of strain and temperature of the two fibers. Nevertheless, this approach is susceptible to measurement errors according to the second type of error described above, i.e., errors associated with measurements at differing locations on the two fibers.

A one-fiber based method has also been attempted to address BFS-related measurement errors. In particular, a fiber with multiple Brillouin peaks is used as the sensing fiber. The different dependencies of the BFS peaks are used by this approach to discriminate between temperature and strain. However, this method, which depends on an evaluation of multiple BFS peaks of the fiber, leads to poor spatial resolution, limited sensing accuracy, and short sensing distance.

There is therefore a need for a Brillouin fiber sensor system capable of both improved spatial resolution and accurate, simultaneous measurements of temperature and strain.

SUMMARY

According to one embodiment, a Brillouin distributed fiber sensor is provided. The fiber sensor includes an optical fiber with a first core, a second core, and a cladding surrounding the cores. Each core is configured to produce a Brillouin frequency shift of at least 30 Mhz relative to the other core.

According to another embodiment, a distributed fiber sensor system is provided. The fiber sensor system includes an optical fiber having a first and a second core. Each core is configured to produce a Brillouin frequency shift of greater than 30 Mhz relative to the other core. The system further includes at least one pump laser configured to launch test light into the optical fiber. The system additionally includes a receiver element configured to receive a Brillouin scattered component of test light from each core and evaluate the Brillouin frequency shift of each core based at least in part on the received test light.

According to a further embodiment, a distributed fiber sensor system is provided. The fiber sensor system includes an optical fiber having a first and a second core. Each core is configured to produce a Brillouin frequency shift of at least 30 Mhz relative to the other core. The system further includes at least one pump laser configured to launch pump test light into the optical fiber; and at least one probe laser configured to launch probe test light into the optical fiber. The system additionally includes a receiver element configured to receive pump and probe test light from each core and evaluate the Brillouin frequency shift for each core based at least in part on the received test light.

Additional features and advantages will be set forth in the detailed description which follows, and in part will be readily apparent to those skilled in the art from that description or recognized by practicing the embodiments as described herein, including the detailed description which follows, the claims, as well as the appended drawings.

It is to be understood that both the foregoing general description and the following detailed description are merely exemplary, and are intended to provide an overview or framework to understanding the nature and character of the claims. The accompanying drawings are included to provide a further understanding, and are incorporated in and constitute a part of this specification. The drawings illustrate one or more embodiments, and together with the description serve to explain principles and operation of the various embodiments.

DETAILED DESCRIPTION

Figure 1:
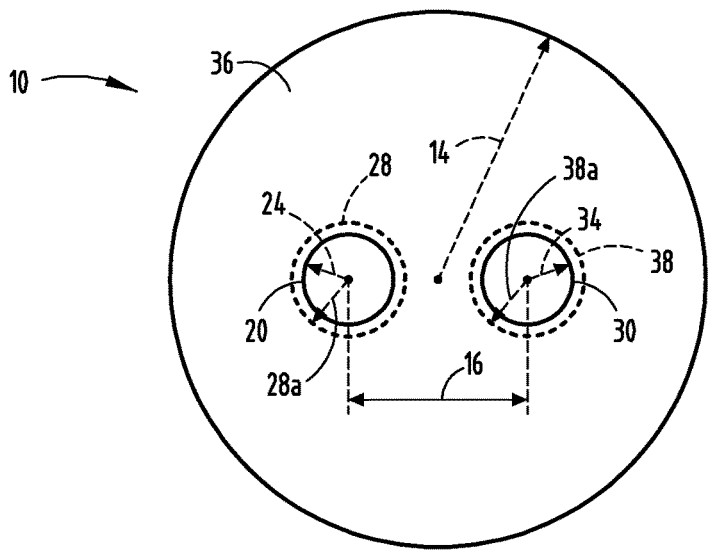
FIG. 1 depicts a cross-section of a two-core optical fiber according to one embodiment.

Reference will now be made in detail to the present preferred embodiments, examples of which are illustrated in the accompanying drawings. Whenever possible, the same reference numerals will be used throughout the drawings to refer to the same or like parts.

A two-core optical fiber-based approach has been developed to remedy the foregoing problems and BFS-related measurement errors. By properly designing the fiber profiles, choosing certain material compositions, and/or doping concentrations of the two fiber cores, each core can be configured with very different Brillouin properties. These modifications can produce Brillouin frequency shift differences of at least 30 Mhz between the cores. As a result of the different temperature and strain coefficients between the two fiber cores, it is possible to make simultaneous temperature and strain measurements by measuring the BFSs of the two fiber cores. The net result is an approach that allows for the simultaneous measurement of strain and temperature with high spatial resolution and sensing accuracy.

In the discussion below, the following definitions and terminology as commonly used in the art are employed.

Refractive index profile: the refractive index profile is the relationship between the relative refractive index percent ($\Delta\%$) and the optical fiber radius r (as measured from the centerline of the optical fiber) over a selected segment of the fiber.

Relative refractive index percent $\Delta(\%)$ or $\Delta$: the term $\Delta$ represents a relative measure of refractive index defined by the equation: $\Delta(\%)=100\times(n_i^2-n_c^2)/2n_i^2$ where $n_i$ is the maximum refractive index of the index profile segment denoted as i, and $n_c$, the reference refractive index. Every point in the segment has an associated relative refractive index measured relative to the reference refractive index.

In a single mode optical fiber, the BFS, $v_B$, is temperature and strain dependent as a result of the thermal expansion and deformation experienced by the fiber. As such, the BFS, $v_B$, changes with temperature and strain. The change of BFS ($\Delta v_B$) as a function of strain variation ($\Delta\epsilon$) and temperature variation ($\Delta T$) can be written as:

$$\Delta v_B = K_\epsilon \Delta\epsilon + K_T \Delta T \qquad (1)$$

where $K_\epsilon$ and $K_T$ are the strain and temperature coefficients of the fiber, respectively. Therefore, if temperature (or strain) is fixed, strain (or temperature) at different locations can be evaluated by measuring the change in BFS, $\Delta v_B$, at the corresponding locations. However, as shown in Equation (1), it is impossible to distinguish either temperature or strain from the BFS if both temperature and strain changes at a sensing location. This is because the change in BFS, $\Delta v_B$, depends on both strain and temperature.

According to one embodiment, a two-core optical fiber 10 is used as a sensing fiber in a Brillouin effect-based distributed fiber sensor. Each fiber core 20, 30 within the fiber 10 is configured in a single mode at the operation wavelength of the Brillouin sensor. Further, each core 20, 30 possesses a single BFS peak. The two fiber cores 20, 30, however, possess different Brillouin frequency shifts. These shifts can be produced by modifying the fiber refractive index profiles, material compositions, and/or doping concentration of the two fiber cores 20, 30. In particular, the BFS dependencies of each fiber core with respect to strain variation ($\Delta\epsilon$) and temperature variation ($\Delta T$) can be written as, respectively:

$$\Delta v_B^{c1} = K_\epsilon^{c1}\Delta\epsilon + K_T^{c1}\Delta T \qquad (2)$$

$$\Delta v_B^{c2} = K_\epsilon^{c2}\Delta\epsilon + K_T^{c2}\Delta T \qquad (3)$$

where $K_\epsilon^{c1}$ and $K_T^{c1}$ are the strain and temperature coefficients of the fiber core 1 (e.g., core 20), respectively, and $K_\epsilon^{c2}$ and $K_T^{c2}$ are the strain and temperature coefficients of the fiber core 2 (e.g., core 30), respectively.

By solving Equations (2) and (3), the strain and temperature variations are given by Equation (4) below:

$$\begin{bmatrix}\Delta\varepsilon\\\Delta T\end{bmatrix} = \frac{1}{K_\varepsilon^{c1}K_T^{c2}-K_\varepsilon^{c2}K_T^{c1}}\begin{bmatrix}K_T^{c2} & -K_T^{c1}\\-K_\varepsilon^{c2} & K_\varepsilon^{c1}\end{bmatrix}\begin{bmatrix}\Delta v_B^{c1}\\\Delta v_B^{c2}\end{bmatrix} \qquad (4)$$

According to one embodiment, a two-core fiber (e.g., fiber 10) can be designed to let $K_\epsilon^{c1}K_T^{c2} \neq K_\epsilon^{c2}K_T^{c1}$. A solution therefore exists for the matrix Equation (4) with such a fiber. With this fiber, it is therefore possible to obtain simultaneous measurements of strain and temperature by monitoring the BFSs of the two fiber cores (e.g., cores 20, 30).

As shown in FIG. 1, a cross-section of a two-core optical fiber 10 with radius 14 is provided. Fiber 10 contains two cores, core 20 and 30, and a cladding 36 surrounding the cores 20 and 30. Core 20 has a radius 24; and core 30 has a radius 34. The two cores 20 and 30 are separated by a distance 16 within optical fiber 10. Cores 20 and 30 may also be surrounded by a low refractive index ring 28 and 38 with a radius 28a and 38a, respectively. Further, cores 20 and 30 are designed with varying refractive profiles such that the Brillouin frequency shift of each core is different than the Brillouin frequency shift of the other. Preferably, the absolute value of the difference between the Brillouin frequency shifts of the two cores 20 and 30 is at least 30 Mhz. More preferably, this difference is at least 80 Mhz. Even more preferably, the difference equals or exceeds 100 Mhz.

Figure 2A:
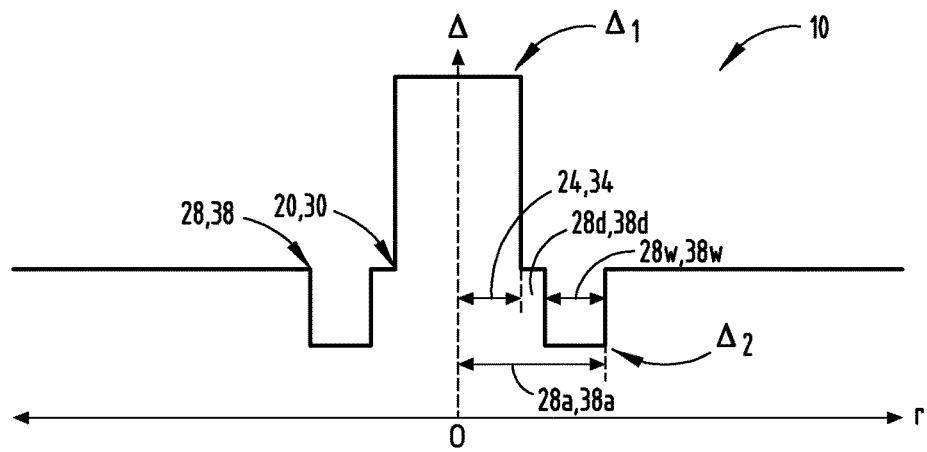
FIG. 2A depicts a step-shaped refractive index profile for one core of a two-core optical fiber according to another embodiment.
Figure 2B:
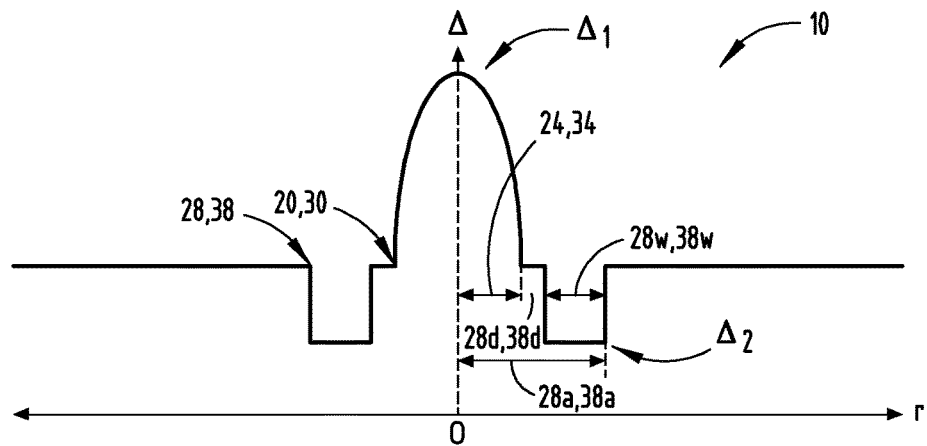
FIG. 2B depicts a graded refractive index profile for one core of a two-core optical fiber according to a further embodiment.

FIGS. 2A and 2B depict the relative refractive index percent, $\Delta$, vs. radius, r, for a core 20, 30 within the two-core optical fiber 10. Cores 20 and 30 can have a simple step index profile (see FIG. 2A) or a graded index profile (see FIG. 2B). The low refractive index ring 28, 38 can also be placed in the cladding 36 of fiber 10 to increase light confinement in either or both of cores 20 and 30. The maximum refractive index of the core 20, 30 is greater than the maximum refractive index of the cladding 36. Preferably, the relative refractive index of the core to the cladding, $\Delta_1$, is greater than 0.2%. More preferably, the relative refractive index, $\Delta_1$, is greater than 0.3%, for example, between 0.3% to 2%.

The core radius 24 and 34 (for cores 20 and 30) are selected in the range of 3 to 10 µm. This ensures that core 20 and 30 are in a single mode at an operating wavelength, for example 1550 nm. The low refractive index ring 28, 38 has a relative refractive index, $\Delta_2$, in the range of −0.7% to −0.1%, and a width 28w, 38w in the range of 1 to 6 µm. This low index "trench" can be offset by a distance 28d, 38d from the outer diameter of core 20 and/or 30. Preferably, the offset 28d, 38d is between 0 to 5 µm.

The distance 16 between the two cores 20 and 30 is greater than 25 µm to minimize the cross talk between them. More preferably, distance 16 is greater than 30 µm. Even more preferably, distance 16 exceeds 40 µm. The diameter of fiber 10 may be 1000 µm or less (i.e., radius 14 is 500 µm or less). Preferably, the diameter of fiber 10 is 200 µm or less (i.e., radius 14 is 100 µm or less). More preferably, the diameter of fiber 10 is 150 µm or less. For example, the diameter of fiber 10 may be set at 125 µm.

For practical sensing applications, it is desirable to ensure low crosstalk between two neighboring cores (e.g., cores 20 and 30) to ensure good system performance. The crosstalk may be −20 dB/km or less. Preferably, the crosstalk is less than −30 dB/km. More preferably, the amount of crosstalk is less than −35 dB/km. Even more preferably, the crosstalk is less than −40 dB/km.

A two-core fiber 10 according to one embodiment can be designed by calculating the optical and acoustic properties of the two cores 20 and 30. The optical field and longitudinal acoustic fields are governed by similar types of scalar wave equations. Accordingly, Equations (5) and (6) can be written in the same form for the fundamental optical mode and the acoustic mode with no azimuthal variations:

$$\frac{d^2 f_o}{dr^2} + \frac{1}{r}\frac{df_o}{dr} + k_o^2(n_0^2(r) - n_{oeff}^2)f_o = 0 \quad (5)$$

$$\frac{d^2 f_a}{dr^2} + \frac{1}{r}\frac{df_a}{dr} + k_a^2(n_a^2(r) - n_{aeff}^2)f_a = 0 \quad (6)$$

where the subscript o stands for the optical field, subscript a stands for the acoustic field, and r corresponds to the radius of fiber 10. For an optical mode, $f_o(r)$ is the optical field distribution, $n_o(r)$ describes the refractive index as a function of the radial position, and $k_o$ is the optical wave number, which is linked to the optical wavelength λ by 2π/λ. For an acoustic mode, $f_a(r)$ is the acoustic field distribution, $n_a(r)$ describes the refractive index as a function of radial position, r, and $k_a$ is the acoustic wave number. In addition, $n_{oeff}$ and $n_{aeff}$ are the effective optical refractive index and effective longitudinal acoustic refractive index, respectively.

The acoustic refractive index is thus defined according to Equations (7) and (8) as:

$$n_a(r) = \frac{V_{clad}}{V_L(r)}, \quad (7)$$

and $$k_a = \frac{2\pi}{\lambda/(2n_{oeff})} = \frac{2\pi}{\lambda'} \quad (8)$$

where λ' is the acoustic wavelength. In Equation (7), $V_{clad}$ is the longitudinal acoustic velocity in the cladding, and $V_L(r)$ describes the longitudinal acoustic velocity as a function of radial position r. Further, the effective longitudinal acoustic index $n_{aeff}$ is related to the effective longitudinal velocity $V_{eff}$ and the longitudinal acoustic velocity in the cladding $V_{clad}$ by Equation (8a) below:

$$n_{aeff} = V_{clad}/V_{eff} \quad (8a)$$

In practice, the (optical) refractive index profile, $n_o(r)$, is often described by the optical delta profile (optical refractive index delta profile), $\Delta_o$. Similarly, it is possible to define the delta (relative refractive index) for the acoustic refractive index, $\Delta_a$, such that each optical refractive index profile, $n_o(r)$, is also associated with a corresponding acoustic delta profile, $n_a(r)$, that describes the acoustic behavior of the longitudinal acoustic field. Using the index definitions for the optical and acoustic waves, the optical delta profile, $\Delta_o$, and acoustic delta profiles, $\Delta_a$, can be described using Equations (9) and (10) as follows:

$$\Delta_o = \frac{n_o^2(r) - n_{oc}^2}{2n_o^2(r)} \times 100\% \quad (9)$$

$$\Delta_a = \frac{n_a^2(r) - n_{ac}^2}{2n_a^2(r)} \times 100\%, \quad (10)$$

where subscript o stands for optical wave, subscript a stands for acoustic wave, and subscript c denotes the refractive index for the cladding.

The optical refractive index of Ge- and F-doped silica glass, $n_o(w_{Ge}, w_F)$, as a function of the Ge and F doping concentration, is described by Equation (11):

$$n_o(w_{Ge}, w_F) = n_o(1 + 1.0 \times 10^{-3} w_{Ge} - 3.3 \times 10^{-3} w_F) \quad (11)$$

where $w_{Ge}$ is the mole percent of the $GeO_2$ dopant, and $w_F$ is the mole percent of the F dopant. The $GeO_2$ dopant contributes to an increase in the refractive index from that of pure silica, and the F dopant contributes to a decrease in the refractive index from that of the pure silica.

Similarly, the role of the Ge and F doping on the acoustic refractive index $n_a(w_{Ge}, w_F)$, can be expressed by Equation (12):

$$n_a(w_{Ge}, w_F) = 1 + 7.2 \times 10^{-3} w_{Ge} + 2.7 \times 10^{-3} w_F \quad (12)$$

As such, Equations (11) and (12) demonstrate that the Ge dopant increases both the optical and acoustic refractive index in the cores 20 and 30 of fiber 10. For example, cores 20 and 30 may be doped with 1 to 10 mol % $GeO_2$ to produce this effect. On the other hand, the F dopant decreases the optical index, while increasing the acoustic index.

For a given dopant profile, an effective refractive index $n_{oeff}$ of a guided optical mode and an effective longitudinal velocity $V_{eff}$ of a guided acoustic mode can be obtained by solving Equations (5) through (8a). The relationship between the effective longitudinal acoustic index $n_{aeff}$ and the effective longitudinal velocity $V_{eff}$ is described earlier. Accordingly, the Brillouin frequency shift, $V_B$, is thus calculated by Equation (13) below:

$$v_B = \frac{2n_{aeff}V_{eff}}{\lambda} \quad (13)$$

Table One below outlines various, modeled parameters for two-core fiber 10 in five design examples. Using the equations discussed above, Brillouin frequency shift values are calculated and listed in Table One for these five two-core fiber design examples. Example 1 has two cores, each with a step index (see, e.g., FIG. 2A), and a core spacing of 50 µm. The two cores (cores 1 and 2) are doped with 3.41 and 4.6 mol % $GeO_2$, respectively. Both cores are single mode at 1550 nm. The mode-field diameters (MFDs) for cores 1 and 2 are 10.3 and 9.2 µm, respectively. The difference in Brillouin frequency shift for these cores is 72.5 Mhz.

In Example 2, core 1 is the same as core 1 from Example 1. However, the core 2 in Example 2 has a higher $GeO_2$ doping level of 5.5 mol %. As a result, the difference in Brillouin frequency shift between these cores is 111.8 Mhz, larger than that estimated in Example 1. Because of larger core delta differences (i.e., differences in relative refractive index) between the cores in Example 2, the cores can be placed closer together.

The two-core fibers simulated in Examples 3 and 4 have graded index profiles (see, e.g., FIG. 2B). With a graded index design, the MFD is larger for the same core delta levels. However, the Brillouin frequency shift is also smaller for these two-core fiber designs.

The two-core fiber outlined in Example 5 in Table One possesses cores with step index profiles comparable to the cores in the fiber exhibited by Example 1. However, the two-core fiber of Example 5 also has a low index ring 28, 38 in the cladding encapsulating the cores. This low index ring improves the light confinement, thereby reducing the bending loss. Further, it allows the cores to be placed closer together in the fiber. In Example 5, the core spacing is reduced to 40 µm. Finally, it should be noted that for all Examples, the difference in Brillouin frequency shift between the cores is at least 30 Mhz.

analyzes it to determine the Brillouin frequency shift associated with cores 120 and 130.

Figure 3A:
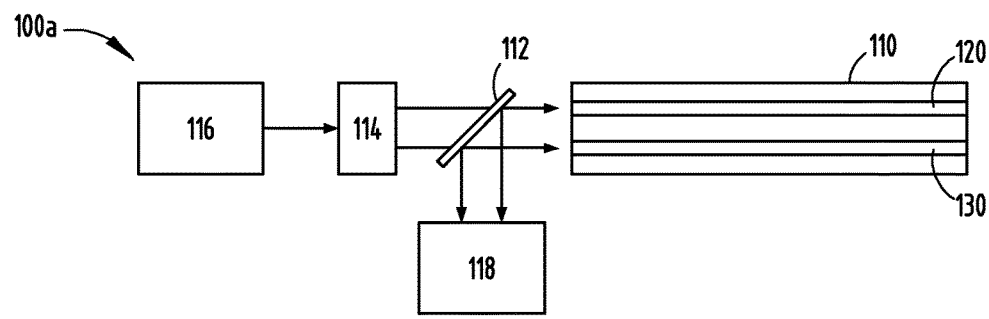
FIG. 3A provides a schematic of a Brillouin Optical Time Domain Reflectometry (BOTDR) fiber sensor using a two-core fiber according to another embodiment.
Figure 3B:
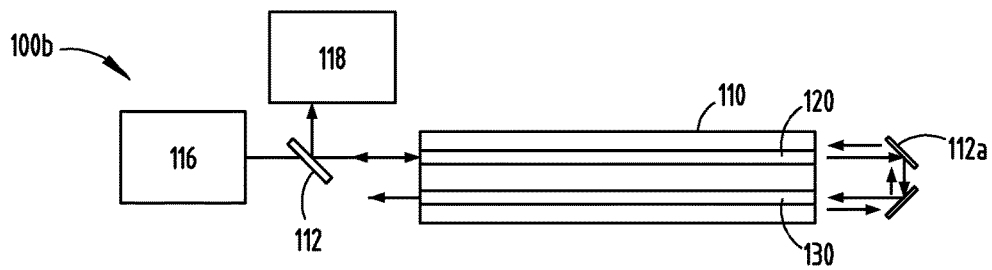
FIG. 3B provides a schematic of a BOTDR fiber sensor using a two-core fiber according to a further embodiment.

In a further embodiment, FIG. 3B depicts a BOTDR fiber sensor system 100b, which operates in a fashion similar to the system 100a depicted in FIG. 3A. As shown in FIG. 3B, pump light from laser 116 is launched through a mirror 112 (e.g., a one-way mirror) into core 120 from one end of the fiber 110. Cores 120 and 130 are coupled together at the other end of fiber 110 by virtue of another mirror, mirror 112a. Mirror 112a, alternatively, may be replaced by other types of known external loop devices. As such, the light from laser 116 travels through core 120, and then loops through core 130. Brillouin scattering light from within both cores 120 and 130 travels back through core 120, impinges mirror 112, and is then detected by photodetector element 118. Note that light traveling through core 130 does not impinge mirror 112. The photodetector element 118 then conducts signal processing on the Brillouin scattered beam, and analyzes it to determine the Brillouin frequency shift associated with cores 120 and 130.

Figure 4A:
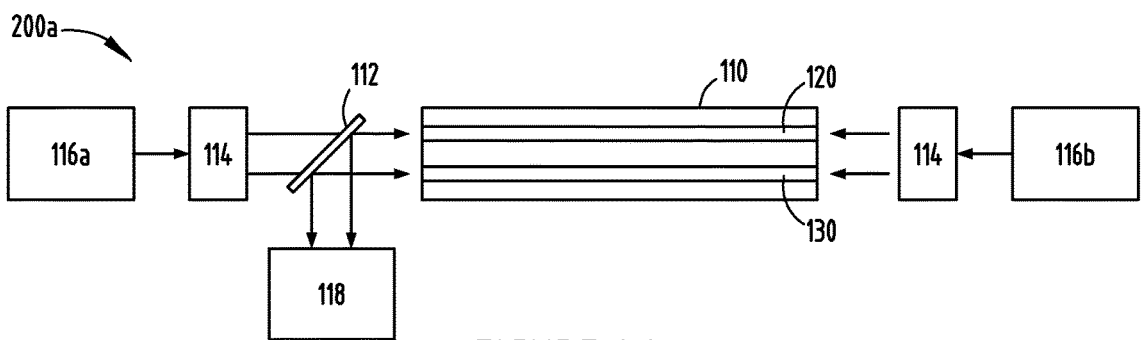
FIG. 4A provides a schematic of a Brillouin Optical Time Domain Analysis (BOTDA) fiber sensor using a two-core fiber according to another embodiment.

In another embodiment, a BOTDA fiber sensor system 200a is depicted schematically in FIG. 4A. Here, probe light from laser 116a is launched into both fiber cores 120 and 130 from one end of fiber 110 through a mirror 112 (e.g., a one-way mirror). At the same time, pump light from laser 116b is launched into both fiber cores 120 and 130 from the

TABLE ONE

|  | Example 1 | | Example 2 | | Example 3 | | Example 4 | | Example 5 | |
| --- | --- | --- | --- | --- | --- | --- | --- | --- | --- | --- |
|  | Core 1 | Core 2 | Core 1 | Core 2 | Core 1 | Core 2 | Core 1 | Core 2 | Core 1 | Core 2 |
| Core spacing (µm) | 50 | | 45 | | 55 | | 47 | | 40 | |
| Core $GeO_2$ (mol %) | 3.41 | 4.6 | 3.41 | 5.5 | 4.1 | 4.6 | 4.1 | 5.5 | 3.41 | 5.5 |
| Optical core delta (%) | 0.34 | 0.46 | 0.34 | 0.55 | 0.41 | 0.46 | 0.41 | 0.55 | 0.34 | 0.55 |
| Acoustic core delta (%) | 2.4 | 3.21 | 2.4 | 3.81 | 2.87 | 3.21 | 2.87 | 3.81 | 2.4 | 3.81 |
| Core radius (µm) | 4.2 | 4.2 | 4.2 | 3.9 | 5.8 | 6.2 | 5.8 | 5.6 | 4.5 | 4 |
| Core alpha | 200 | 200 | 200 | 200 | 2 | 2 | 2 | 2 | 200 | 200 |
| Ring F (mol %) | 0 | 0 | 0 | 0 | 0 | 0 | 0 | 0 | 1.51 | 0.91 |
| Optical ring delta (%) | 0 | 0 | 0 | 0 | 0 | 0 | 0 | 0 | −0.5 | −0.3 |
| Acoustic ring delta (%) | 0 | 0 | 0 | 0 | 0 | 0 | 0 | 0 | 0.41 | 0.25 |
| Ring offset d (µm) | na | na | na | na | na | na | na | na | 5.4 | 4.8 |
| Ring width (µm) | na | na | na | na | na | na | na | na | 3.7 | 5.28 |
| Cutoff (nm) | 1322 | 1532 | 1322 | 1516 | 1354 | 1531 | 1354 | 1513 | 1336 | 1519 |
| MFD (µm) | 10.3 | 9.2 | 10.3 | 8.4 | 10.4 | 10.1 | 10.4 | 9.2 | 10.2 | 8.5 |
| Effective area (µm$^2$) | 81.8 | 67.4 | 81.8 | 55.9 | 81 | 76.9 | 81 | 63.9 | 82.3 | 57.9 |
| Dispersion (ps/nm/km) | 16.5 | 17.5 | 16.5 | 16.4 | 16.7 | 17.7 | 16.7 | 16.7 | 19.5 | 18.2 |
| Brillouin frequency shift (Mhz) | 10816.7 | 10744.2 | 10816.7 | 10704.9 | 10795.7 | 10765.2 | 10795.7 | 10729 | 10816.9 | 10705 |
| Delta Brillouin frequency shift, $\Delta v_B$ (Mhz) | 72.5 | | 111.8 | | 30.5 | | 66.7 | | 111.9 | |

The foregoing two-core optical fibers can be employed in various Brillouin fiber sensor system configurations for the purpose of simultaneous measurement of temperature and strain effects. Exemplar configurations are depicted in FIGS. 3A, 3B, 4A and 4B. One such embodiment, as shown in FIG. 3A, is a BOTDR fiber sensor system 100a. System 100a includes a two-core fiber 110 having two cores, 120 and 130, and a laser 116 (e.g., a pump light laser). Laser 116 launches pump light into beam splitter 114, thus splitting the incident light into two beams. The two split beams are then directed through a mirror 112 (e.g., a one-way mirror) into one end of fiber 110 and, more specifically, into cores 120 and 130. Brillouin scattering light from within cores 120 and 130 impinges the mirror 112 in the reverse direction from the incident light and is then detected by photodetector element 118 (or a pair of photodetector elements 118, associated with cores 120 and 130). The photodetector element 118 conducts signal processing on the Brillouin scattered beam, and other end of fiber 110. As shown in FIG. 4A, the light from lasers 116a and 116b is split into two beams corresponding to cores 120 and 130 with the beam splitter elements 114. These split beams are then directed into cores 120 and 130 from both ends of fiber 110. The transmitted light within cores 120 and 130 is then reflected against mirror 112 and photodetector element 118 (or a pair of photodetector elements 118 corresponding to cores 120 and 130) is used to detect the beams. Photodetector element 118 then analyzes the data to determine the Brillouin frequency shift associated with cores 120 and 130.

Figure 4B:
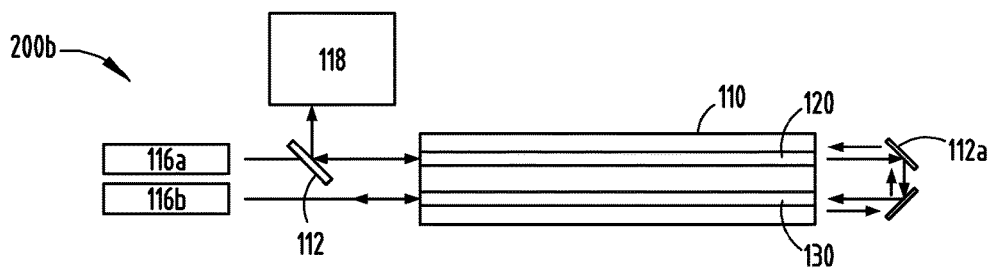
FIG. 4B provides a schematic of a BOTDA fiber sensor using a two-core fiber according to an additional embodiment.

A still further embodiment is depicted in FIG. 4B for BOTDA fiber sensor system 200b. Probe light from lasers 116a and 116b is launched through a mirror 112 (e.g., a one-way mirror) into both fiber cores 120 and 130, respectively, from one end of fiber 110. More specifically, probe light transmitted through the core 120 from laser 116a emanates from the other end of fiber 110 and is reflected back through core 130 by virtue of mirror element 112a. Similarly, pump light transmitted through the core 130 from laser 116b emanates from the other end of fiber 110 and is reflected back through core 120. Transmitted light within cores 120 and 130 travels back through core 120, is then reflected against mirror 112 and, as with configurations 100a, 100b and 200a, photodetector element 118 is used to detect the reflected beam. Again, note that light traveling through core 130 does not impinge mirror 112. Photodetector element 118 then analyzes the data to determine the Brillouin frequency shift associated with cores 120 and 130.

Figure 5:
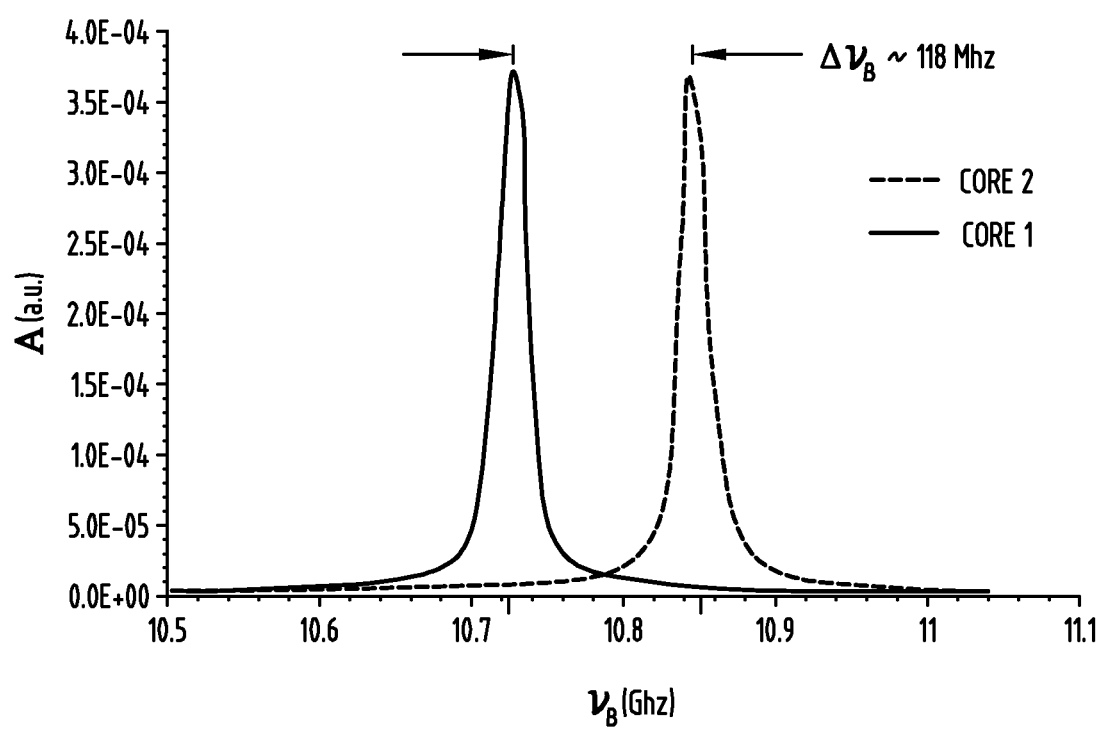
FIG. 5 provides a plot of the measured Brillouin frequency shift for each core in a two-core optical fiber according to another embodiment.

As outlined below in Table Two, a two-core fiber 10 has been manufactured with two cores, each with a measured radius of 4.65 μm and a fiber diameter of 125 μm. Both cores have a step-shaped refractive index profile (see, e.g., FIG. 2A), and a measured core spacing of 55.5 μm. The two cores 1 and 2 are doped with 5.0 and 3.4 mol % $GeO_2$, respectively. The MFDs calculated for these cores are 9.3 and 10.4 μm, respectively. Brillouin frequency shift values of 10.73 and 10.85 Ghz were measured for cores 1 and 2, respectively. FIG. 5, in particular, depicts a Brillouin spectrum for each core of the fiber 10 (as outlined in Table Two), demonstrating the origin of these frequency shift values. Accordingly, the measured change in BFS, $\Delta v_B$, for this two-core fiber is 118 Mhz (see also FIG. 5). Furthermore, the 118 Mhz measured change in BFS, $\Delta v_B$, is comparable to the 111.8 and 111.9 Mhz calculated values for the similarly-structured Example 2 and Example 5 fibers, respectively.

TABLE TWO

| | Manufactured Dual-Core Fiber | |
|---|---|---|
| | Core 1 | Core 2 |
| Core spacing (μm) | 55.5 | |
| Core $GeO_2$ (mol %) | 5.0 | 3.4 |
| Optical core delta (%) | 0.46 | 0.34 |
| Core radius (μm) | 4.65 | 4.65 |
| Fiber diameter (μm) | 125 | |
| Ring F (mol %) | 0 | 0 |
| Optical ring delta (%) | 0 | 0 |
| Cutoff (nm) | 1520 | 1320 |
| MFD (μm) | 9.3* | 10.4* |
| Effective area (μm$^2$) | 68* | 84* |
| Loss @1550 nm (dB/km) | 0.43 | 0.33 |
| Brillouin frequency shift (Mhz) | 10727 | 10845 |
| Delta Brillouin frequency shift, $\Delta v_B$ (Mhz) | 118 | |

Note:
Values denoted in the table above with an asterisk (*) are calculated, not measured The two-core fiber approach can thus be used to improve the accuracy of simultaneous strain and temperature measurements in both BOTDA and BOTDR regimes. Among other benefits, the two-core fiber approach is expected to reduce the installation cost of distributed Brillouin fiber sensors. Further, it will be apparent to those skilled in the art that various modifications and variations can be made without departing from the spirit or scope of the claims.

What is claimed is:

1. An optical fiber comprising:
   a first core, a second core, and a cladding surrounding both of the cores, wherein at least one of the following conditions is satisfied:
   (i) each core is configured with a refractive index profile that is substantially uniform along its length and differs from the refractive index profile of the other core;
   (ii) each core is configured with a doping concentration that differs from the doping concentration of the other core;
   (iii) each core has a different composition than the other core;
   (iv) the optical fiber further comprises a refractive index ring configured to surround at least one of the cores;
   (v) the cores are configured such that the distance between the center of the cores is at least 25 μm; and
   (vi) the cores are configured such that the distance between the center of the cores is at least 25 μm and each core is surrounded by a low refractive index ring;
   wherein each core is configured to exhibit a single Brillouin frequency shift peak (BFS peak) when light is launched into the core, and further wherein the BFS peak of each core differs from the BFS peak of the other core in terms of frequency and each core is configured to exhibit a Brillouin frequency shift of at least 30 Mhz relative to the other core.

2. The fiber according to claim 1, wherein each core is configured to exhibit a Brillouin frequency shift of at least 80 Mhz relative to the other core.

3. The fiber according to claim 1, wherein the optical fiber further comprises a refractive index ring configured to surround at least one of the cores.

4. The fiber according to claim 1, wherein the cores are configured such that the relative refractive index of the cores to the cladding is between about 0.2% to 2%.

5. The fiber according to claim 1, wherein the refractive index profile for each core is selected from the group consisting of step-shaped and graded index profiles.

6. The fiber according to claim 1, wherein each core is doped with germania.

7. The fiber according to claim 6, wherein each core is doped with approximately 1 to 10 mol % germania.

8. The fiber according to claim 3, wherein a trench separates the refractive index ring from the at least one of the cores.

9. The fiber according to claim 1, wherein the cores are further configured such that the distance between the center of the cores is at least 25 μm.

10. The fiber according to claim 6, wherein each core is doped with a different concentration of germania such that the absolute difference in dopant concentration between the cores is about 0.5 mol % or greater.

11. The fiber according to claim 10, wherein each core is doped with a different concentration of germania such that the absolute difference in dopant concentration between the cores is about 1.2 mol % or greater.

12. The fiber according to claim 10, wherein each core is doped with a different concentration of germania such that the absolute difference in dopant concentration between the cores is about 1.6 mol % or greater, and further wherein the cores are configured such that the distance between the center of the cores is about 55 μm and the cladding has an outer diameter of about 125 μm.

13. An optical fiber comprising:
   a first core, a second core, and a cladding surrounding both of the cores, wherein at least one of the following conditions is satisfied:
   (i) each core is configured with a refractive index profile that is substantially uniform along its length and differs from the refractive index profile of the other core;
   (ii) each core is configured with a doping concentration that differs from the doping concentration of the other core;

(iii) each core has a different composition than the other core;
(iv) the optical fiber further comprises a refractive index ring configured to surround at least one of the cores;
(v) the cores are configured such that the distance between the center of the cores is at least 25 µm; and
(vi) the cores are configured such that the distance between the center of the cores is at least 25 µm and each core is surrounded by a low refractive index ring;
wherein each core is doped with a different concentration of germania such that the absolute difference in dopant concentration between the cores is about 0.5 mol % or greater.

14. An optical fiber comprising:
a first core, a second core, and a cladding surrounding both of the cores, wherein at least one of the following conditions is satisfied:
(i) each core is configured with a refractive index profile that is substantially uniform along its length and differs from the refractive index profile of the other core;
(ii) each core is configured with a doping concentration that differs from the doping concentration of the other core;
(iii) each core has a different composition than the other core;
(iv) the optical fiber further comprises a refractive index ring configured to surround at least one of the cores;
(v) the cores are configured such that the distance between the center of the cores is at least 25 µm; and
(vi) the cores are configured such that the distance between the center of the cores is at least 25 µm and each core is surrounded by a low refractive index ring;
wherein each core is doped with a different concentration of germania such that the absolute difference in dopant concentration between the cores is about 1.2 mol % or greater.

15. An optical fiber comprising:
a first core, a second core, and a cladding surrounding both of the cores, wherein at least one of the following conditions is satisfied:
(i) each core is configured with a refractive index profile that is substantially uniform along its length and differs from the refractive index profile of the other core;
(ii) each core is configured with a doping concentration that differs from the doping concentration of the other core;
(iii) each core has a different composition than the other core;
(iv) the optical fiber further comprises a refractive index ring configured to surround at least one of the cores;
(v) the cores are configured such that the distance between the center of the cores is at least 25 µm; and
(vi) the cores are configured such that the distance between the center of the cores is at least 25 µm and each core is surrounded by a low refractive index ring;
wherein each core is doped with a different concentration of germania such that the absolute difference in dopant concentration between the cores is about 1.6 mol % or greater, and further wherein the cores are configured such that the distance between the center of the cores is about 55 µm and the cladding has an outer diameter of about 125 µm.

16. An optical fiber comprising:
a first core, a second core, and a cladding surrounding both of the cores, wherein at least one of the following conditions is satisfied:
(i) each core is configured with a refractive index profile that is substantially uniform along its length and differs from the refractive index profile of the other core;
(ii) each core is configured with a doping concentration that differs from the doping concentration of the other core;
(iii) each core has a different composition than the other core;
(iv) the optical fiber further comprises a refractive index ring configured to surround at least one of the cores;
(v) the cores are configured such that the distance between the center of the cores is at least 25 µm; and
(vi) the cores are configured such that the distance between the center of the cores is at least 25 µm and each core is surrounded by a low refractive index ring;
wherein the fiber is further configured such that crosstalk between the cores is −20 dB/km or less.

17. The fiber according to claim 1, wherein the distance between the center of the cores is at least 40 µm.

18. The fiber according to claim 16, wherein each core is configured to exhibit a single Brillouin frequency shift peak (BFS peak) when light is launched into the core, and further wherein the BFS peak of each core differs from the BFS peak of the other core in terms of frequency.

19. An optical fiber comprising: a first core, a second core, and a cladding surrounding both of the cores, wherein at least one of the following conditions is satisfied:
(i) each core is configured with a refractive index profile that is substantially uniform along its length and differs from the refractive index profile of the other core;
(ii) each core is configured with a doping concentration that differs from the doping concentration of the other core;
(iii) each core has a different composition than the other core;
(iv) the optical fiber further comprises a refractive index ring configured to surround at least one of the cores;
(v) the cores are configured such that the distance between the center of the cores is at least 25 µm; and
the cores are configured such that the distance between the center of the cores is at least 25 µm and each core is surrounded by a low refractive index ring, wherein each core is configured to exhibit a single Brillouin frequency shift peak (BFS peak) when light is launched into the core, and further wherein the BFS peak of each core differs from the BFS peak of the other core in terms of frequency;
wherein each core is configured to exhibit a Brillouin frequency shift of at least 30 Mhz relative to the other core.

20. The optical fiber according to claim 19, wherein the cores are single mode cores at a 1550 nm wavelength.

* * * * *

UNITED STATES PATENT AND TRADEMARK OFFICE
CERTIFICATE OF CORRECTION

PATENT NO. : 9,574,911 B2
APPLICATION NO. : 13/658991
DATED : February 21, 2017
INVENTOR(S) : Brett Jason Hoover et al.

Page 1 of 1

It is certified that error appears in the above-identified patent and that said Letters Patent is hereby corrected as shown below:

On the Title Page

Item [56], in Column 2, Line 2, delete "IEE" and insert -- IET --.

Item [56], in Column 2, Line 35, delete "Enginnering," and insert -- Engineering, --.

Signed and Sealed this
Fourth Day of October, 2022

Katherine Kelly Vidal
*Director of the United States Patent and Trademark Office*